(12) United States Patent
Miyakawa et al.

(10) Patent No.: US 7,259,290 B1
(45) Date of Patent: Aug. 21, 2007

(54) ANIMAL MODEL OF HUMAN HEMATOPOIETIC TUMOR

(75) Inventors: Yoshitaka Miyakawa, Shinjuku (JP); Masahiro Kizaki, Shinjuku (JP); Yasuo Ikeda, Shinjuku (JP); Masato Nakamura, Setagaya (JP); Yasuyuki Ohnishi, Yokohama (JP)

(73) Assignee: Central Institute for Experimental Animals, Kanagawa (JP)

( * ) Notice: Subject to any disclaimer, the term of this patent is extended or adjusted under 35 U.S.C. 154(b) by 56 days.

(21) Appl. No.: 10/533,796

(22) PCT Filed: Nov. 6, 2003

(86) PCT No.: PCT/JP03/14149

§ 371 (c)(1),
(2), (4) Date: May 4, 2005

(87) PCT Pub. No.: WO2004/040970

PCT Pub. Date: May 21, 2004

(30) Foreign Application Priority Data

Nov. 6, 2002 (JP) ............................. 2002-322995

(51) Int. Cl.
*C12N 15/00* (2006.01)
*G01N 33/00* (2006.01)
*A01K 67/033* (2006.01)

(52) U.S. Cl. ................. 800/21; 800/3; 800/8; 435/325
(58) Field of Classification Search .................... 800/3, 800/8, 21, 18; 435/325
See application file for complete search history.

(56) References Cited

U.S. PATENT DOCUMENTS

2003/0182671 A1* 9/2003 Ito et al. ........................ 800/18

FOREIGN PATENT DOCUMENTS

WO  WO 02/43477 A1  6/2002

OTHER PUBLICATIONS

Blase et al. (1995) Int. J. Cancer 60: 860-865.*
Mitsuyoshi Urashima, et al., "The Development of a Model for the Homing of Multiple Myeloma Cells to Human Bone Marrow", BLOOD, American Society of Hematology, vol. 90, No. 2 Jul. 15, 1997; pp. 754-765.
Yoshi Miyakawa, et al., "Establishment of Human Multiple Myeloma Model Using Newly Developed Immunodeficienent NOD/SCID./IL-2Rγ-/- (NOG) Mice", Abstract #2366, Poster Board #-Session 650-II, American Society of Hematology, vol. 100, No. 11 Nov. 16, 2002; pp. 601a.

* cited by examiner

*Primary Examiner*—Michael Wilson
(74) *Attorney, Agent, or Firm*—Ginger R. Dreger, Esq.; James A. Fox, Esq.; Heller Ehrman, LLP

(57) ABSTRACT

Production and utilization of model mouse, in which human hematopoietic tumor cells can be grown, expressing symptom of human hematopoietic tumor, and can be used in the screening of anticancer drugs for human hematopoietic tumor.

The invention provides a new method to produce model mouse for human hematopoietic tumor, including engraftment of human hematopoietic tumor cells into NOG (NOD/Shi-scid, IL-2Rγ KO) mice.

3 Claims, 11 Drawing Sheets
(9 of 11 Drawing Sheet(s) Filed in Color)

ANIMAL MODEL OF HUMAN HEMATOPOIETIC TUMOR

FIELD OF THE INVENTION

This invention is relating to a creation of experimental mouse model of human hematopoietic tumor.

BACKGROUND OF THE INVENTION

Multiple myeloma is one of the hematological malignancies, accompanied by the clonal proliferation of plasma cells. Typical clinical symptoms of the patient with multiple myeloma are anemia, pathological bone fracture, hypercalcemia, renal dysfunction, and reiterating infectious disease, which are caused by proliferation of malignant tumor cells in bone marrow. Chemotherapy or autologous bone marrow transplantation is adopted to prolong the patient's life. However, its prognosis is not satisfactory. Cause of multiple myeloma is yet to be elucidated due to its heterogeneity.

Lymphoma is a kind of hematopoietic tumor associated with abnormal proliferation of lymphoid cells. It is categorized into two classes, Hodgkin's disease with good prognosis and non-Hodgkin's lymphoma with bad prognosis. A new type of animal disease model is essential for new drug development.

Developing successful mouse disease model of human multiple myeloma and human T-cell lymphoma has been a challenge for investigating cause and developing treatment of those diseases for the long time. Several mouse models engrafted human myeloma cells have been reported. However, those methods were extremely complicated. For example, Pilarski et. al. engrafted human multiple myeloma cells into NOD/SCID mice by intra-cardiac injection (Non-patent reference 1). Yaccoby et. al. reported that a partially autonomous growth of human myeloma cells by implanting them into a small piece of human fetal bone, which was engrafted under a mouse skin. In the case of an experiment performed by Tsunenari, they reported about a new xenograft SCID mice model in which human KPMM2 myeloma was engrafted (Non-patent reference 2). However, KPMM2 has been already held in SCID mice as a form of solid tumor and their model does not necessarily represent the pathology of human myeloma. Accordingly, no humanized disease animal model, that can be easily used for the study of pathogenesis and therapy development, has been established based on the existing immune deficient mice.

Non-patent reference 1
Exp Haemat, 30, 221-228, 2002; Blood, 95, 1056-1065, 2000
Non-patent reference 2
Blood, 90, 2437-2444, 1997

SUMMARY OF THE INVENTION

This invention aims to develop a mouse model of human hematopoietic tumor cells, in which human hematopoietic tumor cells can autonomously grow, which exhibits symptoms from human hematopoietic tumor, and which can be used in screening for new drugs to treat human hematopoietic tumor and provide the use of the mouse.

The inventors had already developed immune deficient mouse, NOG mouse (International Patent Publication Number: WO0243477). NOG (NOD/Shi-scid, IL-2Rγ KO) mouse lacks functional T-cell and B-cell, has declined macrophage function, lacks natural killer (NK) cells or its function, is accompanied by impaired dendritic cell function, and has strong heterocytotropic capability. Engrafted human cells can, therefore, autonomously grow at great extent. NOG mouse is more severely immune deficient than other congenitally immune deficient mouse, such as, NOD/Shi-scid mouse or C.B-17-scid mouse. The inventors established a mouse model of human hematopoietic tumor and completed this invention by engrafting human myeloma cell line, U266, which has an interleukin-6 dependency and has a slow regeneration rate and T-cell lymphoma LM-2-JCK, into NOG mouse.

The invention includes:

(1) A method of creating a mouse model of human hematopoietic tumor, comprising a method engrafting human hematopoietic tumor cells to NOG (NOD/Shi-scid, IL-2Rγ KO) mouse.

(2) A method of creating a mouse model of human hematopoietic tumor according to (1) above, whereinhuman hematopoietic tumor cell is human multiple myeloma U266 cell.

(3) A method of creating a mouse model of human hematopoietic tumor according to (1) above, wherein human hematopoietic tumor cell is human T-cell lymphoma, LM-2-JCK.

(4) A NOG (NOD/Shi-scid, IL-2Rγ KO) mouse model in which human hematopoietic tumor cells are engrafted and human hematopoietic tumor is formed.

(5) The mouse according to (4) above, wherein human hematopoietic tumor is human multiple myeloma.

(6) The mouse according to (4) above, wherein human hematopoietic tumor is human T-cell lymphoma.

(7) A screening method of therapeutic agents for human hematopoietic tumor according to (4) above, which comprises administrating a test substances to the human hematopoietic tumor mouse model.

(8) The screening method according to (7) above, wherein human hematopoietic tumor is human multiple myeloma.

(9) The screening method according to (7) above, wherein human hematopoietic tumor is human lymphoma.

The disclosure of Japanese Patent Application No. JP2002-322995 including the specification and drawings is incorporated herein by reference in its entity.

BRIEF DESCRIPTION OF DRAWINGS

The file of this patent contains at least one drawing executed in color. Copies of this patent with color drawing(s) will be provided by the Patent and Trademark Office upon request and payment of the necessary fee.

BEST MODE FOR CARRYING OUT THE INVENTION

Figure 1:
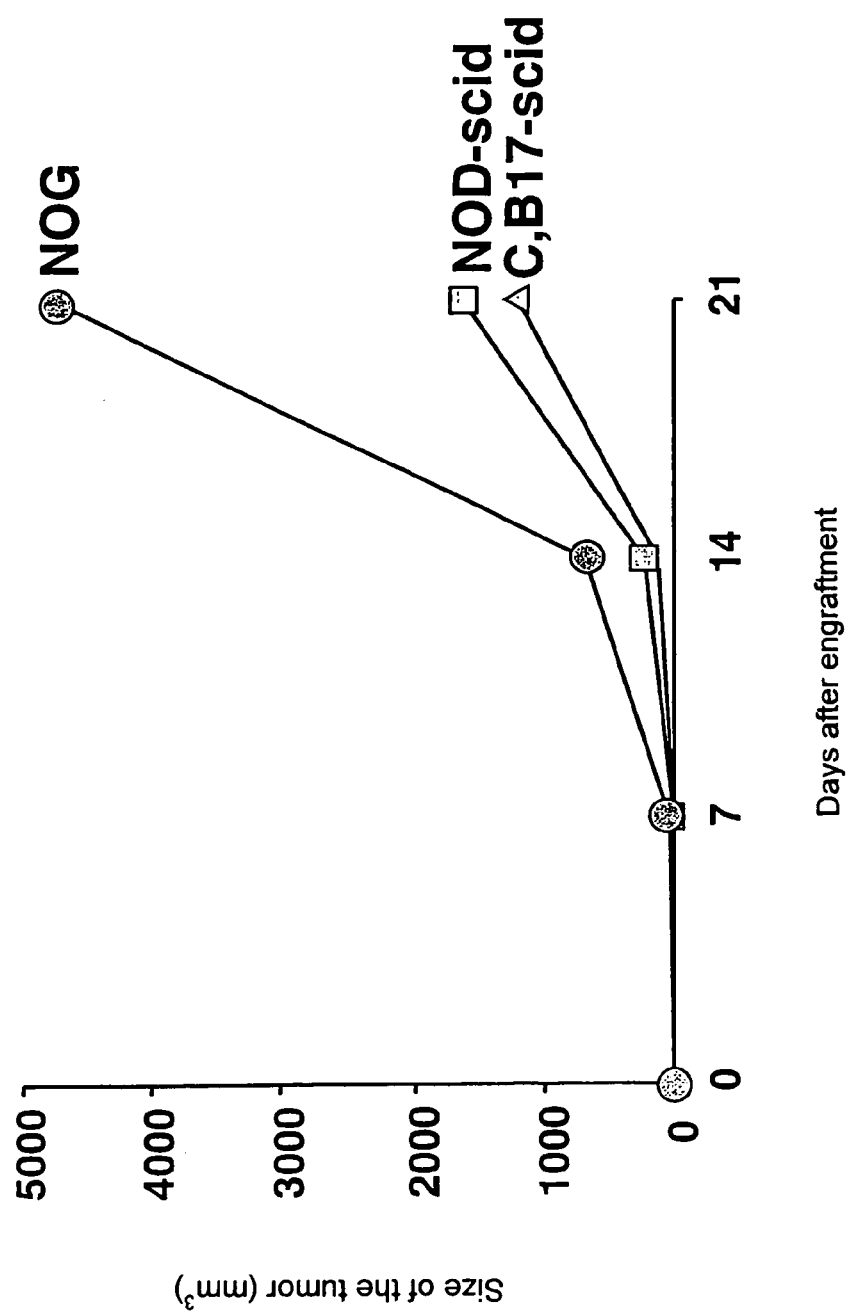
FIG. 1 shows measured tumor size as a function of time after the engraftment of LM-2-JCK cells in mice.

The invention is explained in detail.

1. Production of NOG Mice

NOG mice are produced by the method, explained in the International Publication Number, WO02/43477, and explained as follows.

NOG mice are produced by backcross mating mice B with mice A according to the method explained in the following.

A: Mice that are obtained by backcross mating C.B-17/Icr-scid (C.B-17-scid or CB17/SCID mice) mice with NOD/Shi mice.

B: Mice in which interleukin-2 receptor γ chain is knocked out.

Several different cells were used here including human, mouse, rat, and other mammalian cells and tissues, especially human stem cells, lymphocyte, and cancer cells, but not limited to them.

In order to obtain mice: A, backcross mating of C.B-17/Icr-scid mice with NOD/Shi mice is performed by following a publicly known method, such as, Cross Intercross (Inbred Strains in Biomedical Research, M. F. W. Festing, 1979, ISBN 0-333-23809-5, The Macmillan Press, London and Basingstoke). It is performed as follows. Firstly, C.B-17/Icr-scid mice and NOD/Shi mice are mated. Secondly their F1 mice are mated with each other to obtain F2 mice. Finally, F2 mice that lack immunoglobulin in serum are selected and such F2 mice are mated with NOD/Shi mice again. This procedure is repeated nine times or more (Cross Intercross method) to obtain the mice A.

NOD/Shi mice and C.B-17/Icr-scid mice are both sold by CLEA Japan, Inc. NOD-scid mice, that were established from mating these mice by the inventors (JP publication No. 9-94040), can be obtained from CLEA Japan, Inc., to be used as the mice A as well. Note that the applicants also keep the NOD/Shi mice and NOD-scid mice, and those mice can be distributed through the applicants.

Knocking out of interleukin-2 receptor γ chain in the mice B can be performed by following the publicly known method, for example, homologous recombination using mouse ES cells (Capecchi, M. R., Altering the genome by homologous recombination, Science, (1989) 244, 1288-1292). Such the knockout mice are produced by replacing a target gene in mice with homologous gene including drug-resistant gene, such as neomycin, in the stage of ES cell, and by injecting the ES cell into fertilized egg.

To give an actual example, a gene clone including mouse IL-2Rγ is isolated from the gene library for 129/SV mouse using human IL-2RγcDNA as a probe and a target vector is created using a fragment with a size of 8.6 kb including full length of IL-2Rγ, namely inserting a PMC1-neo poly(A) expressing a neomycin-resistant gene between exon 7 and exon 8 on IL-2R in the fragment and locating a diphtheria toxin-A gene near 3' where 1 kb apart from exon 8. The vector is, then, straightened and inserted into $1\times10^7$ E14 ES cells by electroporation. A homologous recombinant ES clone is selected (to be confirmed by PCR or Southern transfer) in the culture medium including G418, the ES clone is injected into the blastocyst of C57BL/6 mice, and it is transferred into the uterus of foster mice. IL2RγKO hetero mice, in which IL-2Rγ is knocked out from its germ cells, can be finally obtained by mating chimera mice born from the foster mice, with C57BL/6 mice.

Alternatively, established interleukin-2 receptorγchain knockout mouse strain can be purchased directly for this purpose. One of such examples is interleukin-2 receptorγchain knockout mice (Ohbo K, Suda T, Hashiyama M et. al. Modulation of hematopoiesis in mice with a truncated mutant of the interleukin-2 receptor gamma chain. Blood 1996; 87 (3):956-67)) that were produced from IL2RγKO mouse strain (Prof. Kazuo Sugamura, Department of Microbiology and Immunology, Tohoku University Graduate School of Medicine). Note that IL2RγKO mice were transferred to CIEA from the originator, Professor Sugamura, kept in an embryo preservation bank, and obtainable as cryopreserved embryos or mice raised from dissolving cryopreserved embryos when needed.

Furthermore, backcross mating of the mice A with the mice B can be performed by a publicly known method, for example, by mating NOD-scid mice with IL2RγKO mice and backcross mating their F1 mice with NOD-scid mice according to the method explained above.

2. Producing Disease Model Mouse

Human hematopoietic tumor-model mouse can be produced by transplanting human hematopoietic tumor cells to NOG mouse and letting the cells to grow autonomously.

Established cell line or patient specimen is available for hematopoietic tumor, such as, multiple myeloma, lymphoma, leukemia, and myeloproliferative diseases. For example, U266, RPMI8226, IM9, and HS-Sultan are available as cell lines for human multiple myeloma. LM-2-JCK-cell is available in cell line for human lymphoma. These cells can be obtained from ATCC cell bank (US) or JCRB cell bank (Japan). They can be also obtained by a proliferating method explained in the following.

Growth potential of human cells, which were not grown in the known immune deficient mice, in the NOG mice is expected to be significantly high. In addition to human myeloma and lymphoma, disease model mouse by engrafting patient specimens (lymph node, peripheral blood cells, or bone marrow cells) of leukemia, myelodysplastic syndrome, myeloproliferative disease, or autoimmune disease, is also expected to be producible.

Production of the tumor model mouse can be done by engrafting the tumor cell strain to NOG mouse and letting them grow in it. Engraftment of the tumor cell strain can be done by dispersing the tumor cells in physiological saline or similar solutions with appropriate density and by subcutaneously or intravenously injecting them into the mouse body. The best injection method can be adopted according to the species of tumor cell strain.

The number of engrafting cells can be also adjusted according to the species of tumor cell strain and $10^6 \sim 10^7$ cells are usually engrafted into a mouse.

The engrafted cells are grown and human hematopoietic tumor is formed in several weeks to several months after the engraftment. Disease model mouse is, then, established with observable weight loss, tachypnea, paralysis, piloerection, and other relating symptoms.

3. Application of the Disease Model Mouse

Human tumor model mouse can be used to screen anti-cancer, anti-metastatic, and other relating drugs. Efficacy of the drug can be evaluated by measuring tumor size, the number and size of metastasis, and the death/live ratio after orally, intravenously or percutaneously administering the drug to the mice with grown tumor. NOG mice, in which myeloma U266 cells are engrafted, are used to evaluate the efficacy of the anti-cancer drug, doxorubicin. By administering doxorubicin to the mice, the amount of human immune globulin secreted from the engrafted human myeloma cells was reduced by 30% in the mice serum. It is, therefore, established that this method can be used to evaluate the efficacy of anti-cancer drugs and the human tumor model mouse is applicable as therapy model.

Invasion of human tumor cells into bone marrow and spleen in mice can be quantitatively measured by the flow cytometry adopting the antibodies, such as, anti-human CD45 antibody, that specifically responses to the human tumor cells. The histological specimens of each organ can be used to identify the invasion. Human globulin in murine serum can also be detected by the sandwich ELISA method.

EXAMPLE 1

Production of Immune Deficient Mice (NOG Mice) with Eliminated NK Cell Activity and Diminished Dendritic Cell Activity.

Severe combined immunodeficient mice with eliminated NK cell activity were produced by the following procedure. F1 mice, in which a mutated IL-2Rγgene was introduced, were obtained by backcross mating interleukin-2 receptors chain knockout mice (IL-2RγKO mice) (eight-week-old) that was handed over from Prof. Kazuo Sugamura (Department of Microbiology and Immunology, Tohoku University Graduate School of Medicine) with NOD/Shi-scid mice (also obtainable from CLEA Japan, inc.) (eight-week-old) maintained at Central Institute for Experimental Animals (CIEA), Japan. The existence of mutated IL-2Rγ chain gene in the F1 mice was confirmed by genotyping by PCR to detect the target gene. DNA was extracted from the F1 mice blood (100 µL) from the fundus vein, using DNA auto-extraction machine (MagExtractor, TOYOB). The extracted DNA (1.5 µL) was added to the PCR buffer (23.5 µL, 1.5 mM $MgCl_2$ and 0.4 mM dNTP, and 25 pmol) containing two sets of primers (a set of primers, P1 and PIII, were used to identify the wild-type allele, and PI and PII to identify mutant allele), and PCR was carried out under the following reaction conditions to identify wide-type and mutant allele for IL-2Rγ chain gene:

(Primer)

PI: 5'-CTGCTCAGAATGATGCCTCCAATTCC-3' (SEQ ID No: 1)

PII: 5'-CCTGCGTGCAATCCATCTTGTTCAAT-3' (SEQ ID No:2)

PIII: 5'-GATCCAGATTGCCAAGGTGAGTAG-3' (SEQ ID No:3)

(PCR Condition)

After the agent was heated at 94° C. for 5 minutes, PCR was carried out for 30 to 35 cycles (94° C., 1 minute; 55° C., 1 minute; 72° C., 1 minute), and it was kept heated at 72° C. for 10 minutes.

The produced agent from the PCR was examined by electrophoresis in 2% agarose gel and coloring band width was measured after ethidium bromide staining to identity mutant and wild-type alleles. Multiplied fragments to detect the mutant and wild-type alleles were approximately 350 bp and 660 bp, respectively.

(Backcross Mating)

In the next, F2 mice were obtained by backcross mating the F1 mice, in which IL-2Rγ mutant genes were injected, with the NOD/Shi-scid mice. The same PCR method was used to detect IL-2Rγchain mutant gene and a simple immunodiffusion was used to detect serum immunoglobulin. Homozygosity for the scid gene was, then, confirmed. The obtained mice were mated with NOD/Shi-scid mice and litter mice with IL-2Rγchain mutant gene were mated with NOD/Shi-scid mice again.

Figure 11:
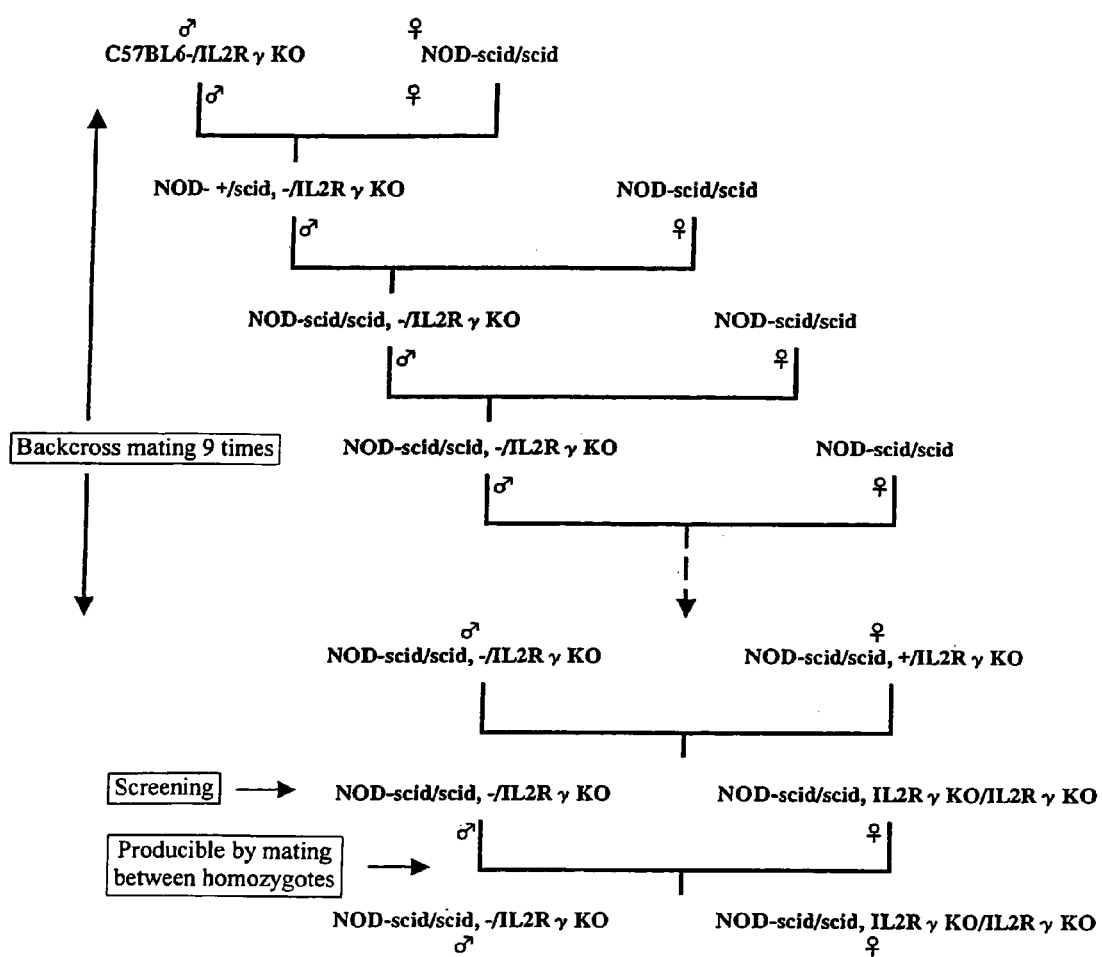
FIG. 11 shows outline of backcross mating to produce NOG mice.

This backcross mating was repeated at least nine times to produce NOG mice (see FIG. 11). It is more effective to use male mice as IL-2RγKO mice, since IL-2Rγ chain gene is on X chromosome.

EXAMPLE 2

Production of Human T-Cell Lymphoma LM-2-JCK Engrafted NOG Mice

NOD/Shi-scid mice and NOG (NOD/Shi-scid, IL-2Rγ KO) mice were obtained from CIEA. BALB/cAJcl-nu mice and C.B-17/Icr-scid mice were obtained from CLEA Japan, Inc. All the mice were five-week-old and maintained under specific pathogen-free conditions.

Human tumor cell strain, LM-2-JCK, for xenograft has been established from lymphoma in thirteen-year-old male patient and maintained by subculture xenograft in nude mice. LM-2-JCK can be obtained from ATCC cell bank (US)

and JCRB cell bank (Japan). T cell antigen, CD4, and CD5 are expressed in LM-2-JCK but B cell antigen, such as, immunoglobulin, is not (Maruo et al., APMIS 101: 345-352, 1993).

LM-2-JCK that had been maintained by subculture xenograft in nude mice was subcutaneously extracted. The extracted LM-2-JCK was cut into small pieces by scissors and diffused in F-10 nutrient mixture culture medium (GIBCO) containing collagenase (SIGMA) 200 U/mL and DNasa (SIGMA) 270 U/mL. The resultant agent was passed through nylon mesh to obtain a uniform cell suspension. The number of live tumor cells in the suspension was counted by staining using a trypan blue (GIBCO BRL). The tumor cell density was adjusted to $1 \times 10^7$ and $1 \times 10^6$ live-cells/mL in physiological saline after centrifugation. The suspension containing tumor cells were subcutaneously injected (0.1 mL) into both flanks of NOG (NOD/Shi-scid, IL-2Rγ KO) mice, NOD/Shi-scid mice, BALB/cAJcl-nu mice, and C.B-17/Icr-scid mice, by using 25 gauge needle. The number of injected locations in each mouse was eight to ten. The size of the tumor and the mice weight were measured once a week after the injection. Engrafted mice were sacrificed when they developed disease symptoms and the size of the tumor was measured. Table 1 shows the number of injected locations, that of tumor developed, and the weight of the tumor.

Icr-scid mice were irradiated with 250 rad before $2 \times 10^6$ U266 cells were intravenously inoculated into them.

The U266 transplanted NOG mice revealed hind leg paralysis, weight loss, piloerection, and tachypnea six weeks after the transplantation. Extensive infiltration of U266 cells into the bone marrow of lumber bones and sternum was observed in the histological studies of the NOG mice but no such infiltration was observed in NOD/Shi-scid mice or C.B-17/Icr-scid mice. Such infiltration of U266 cells into the spinal cavity and disruption of lumber bones in large extent were presumed to be the cause of the observed leg paralysis in NOG mice. Infiltration of the tumor cells was limited in bone marrow and no infiltration to the other organs, such as, liver, spleen, or lung, was observed. By flow cytometry analysis, 80-90% of nucleated cells were found to express human CD45 in the bone marrow of the NOG mice in which U266 cells were transplanted. This indicates that most of the mouse bone marrow cells were replaced by the human bone marrow cells. U266 cells in the murine bone marrow were positive for human IgE in all the five NOG mice, indicating that U266 cells had maintained the production of human IgE in the bone morrow of NOG mice and the NOG mice were to be disease model for multiple myeloma.

Table 2 shows that the engraftment ability of U266 cells in each mouse.

TABLE 1

Xenograft performance of LN-2-JCK in three kinds of mice with different gene background

| Mouse Strain | # of engrafted cells | Observed period | # of tumor developed location/# of injected location | Weight of tumor (a) |
|---|---|---|---|---|
| NOG NOD/Shi-scid, IL-2Rγ KO | $10^6$ | 21 days | 10/10 (100%) | 3.97 ± 2.10 (b) |
| NOD/Shi-scid | $10^6$ | 21 days | 10/10 (100%) | 1.34 ± 0.77 |
| C.B-17/Icr-scid | $10^6$ | 21 days | 8/10 (80%) | 1.21 ± 1.06 |
| NOG NOD/Shi-scid, IL-2Rγ KO | $10^5$ | <9 weeks | 8/8 (100%) (c) | N.T. |
| NOD/Shi-scid | $10^5$ | <9 weeks | 5/10 (50%) | N.T. |
| C.B-17/Icr-scid | $10^5$ | <9 weeks | 0/10 (0%) | N.T. |

Weight of tumor was measured on 21 days after the injection. The measured value is indicated as means ± standard deviation (gram).
The result for NOG mice has the statistical significance with that for NOD/Shi-scid mice and C.B-17/Icr-scid mice (p < 0.05; t-test).
The result for NOG mice has the statistical significance with that for NOD/Shi-scid mice (p < 0.05; chi-square-test) and C.B-17/Icr-scid mice (p < 0.001; chi-square-test).
N.T.: Not Tested FIG. 1 shows measured tumor size as a function of time after the engraftment. As shown in this figure, the size of tumor in NOD/Shi-scid mice and C.B-17/Icr-scid mice on 21 days after the engraftment are small but that in NOG mice are significantly larger.

LM-2-JCK cells were grown faster in NOG mice than in NOD/Shi-scid mice, BALB/cAJcl-nu mice, and C.B-17/Icr-scid mice.

EXAMPLE 3

Production of NOG Mice with Human Multiple Myeloma U266 Cells Engrafted.

U266 cell line was obtained from ATCC cell bank (US). Ten NOG mice, ten NOD/Shi-scid mice, and ten C.B-17/

TABLE 2

Xenograft performance of human myeloma cell, U266, in three kinds of immune deficient mice with different gene background

| | Infiltration of U266 myeloma cells | | | | | |
|---|---|---|---|---|---|---|
| | Bone Marrow | | | Other Organs | | |
| Mouse Strain | Femur | Spine | Sternum | Spleen | Liver | Lung |
| NOG NOD/Shi-scid, IL-2Rγ KO | 5/5* | 5/5 | 5/5 | 0/5** | 0/5 | 0/5 |

TABLE 2-continued

Xenograft performance of human myeloma cell, U266, in three kinds of immune deficient mice with different gene background

| | Infiltration of U266 myeloma cells | | | | | |
|---|---|---|---|---|---|---|
| | Bone Marrow | | | Other Organs | | |
| Mouse Strain | Femur | Spine | Sternum | Spleen | Liver | Lung |
| NOD/Shi-scid | 0/5 | 0/5 | 0/5 | 0/5 | 0/5 | 0/5 |
| C.B-17/Icr-scid | 0/5 | 0/5 | 0/5 | 0/5 | 0/5 | 0/5 |

*Apparent infiltration of myeloma cells and necrosis with fibrinogenesis was observed in bone marrow of femur.
**Significant increase of megakaryocyte was observed. This indicates blood-forming outside of bone marrow.

As shown in table 2, infiltration of U266 cells into the bone marrow of the NOG mice was observed, but no infiltration were observed into spleen, liver, or lung. Such infiltration into bone marrow, spleen, liver, or lung of the NOD/Shi-scid mice or C.B-17/Icr-scid mice was not observed, either.

Figure 2:
FIG. 2 shows histological analyses of infiltrated lesions of the NOG mice with U266 cells engrafted (magnified by 5.3 times).
Figure 3:
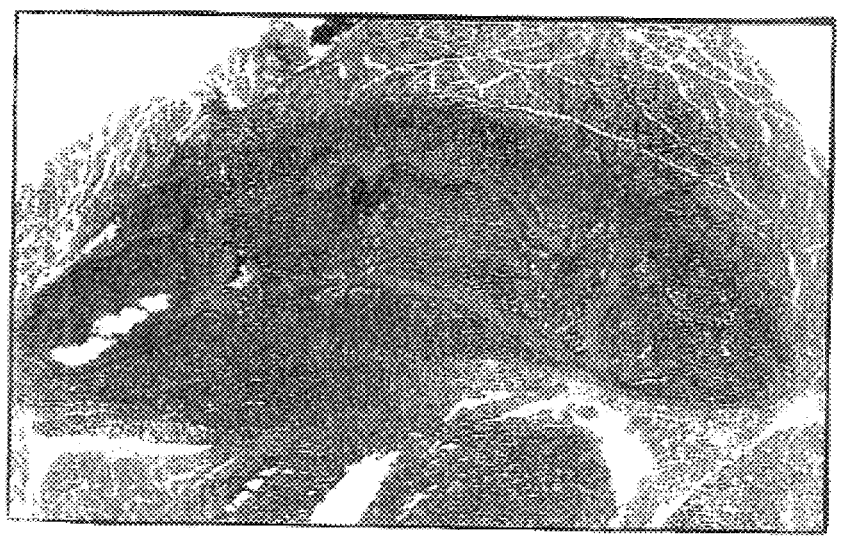
FIG. 3 shows histological analyses of infiltrated lesions of the NOG mice with U266 cells engrafted (magnified by 12 times).
Figure 4:
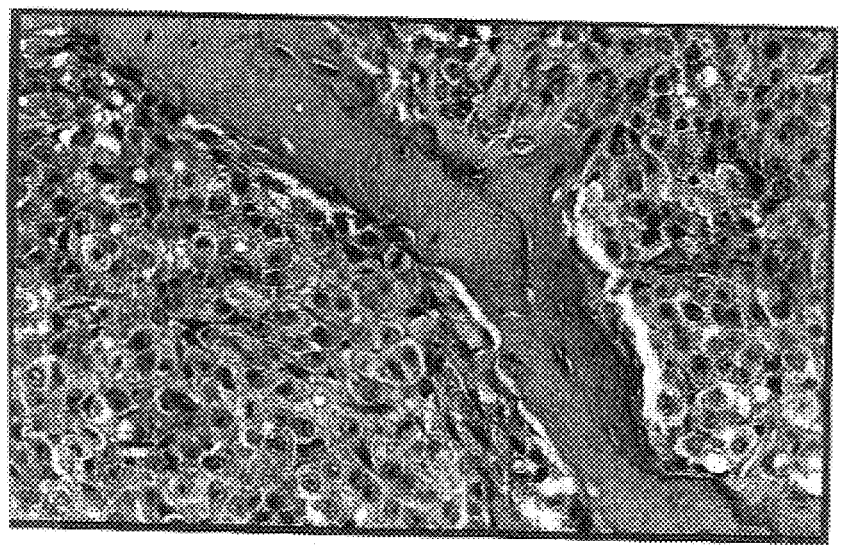
FIG. 4 shows histological analyses of infiltrated lesions of the NOG mice with U266 cells engrafted (magnified by 100 times).
Figure 5:
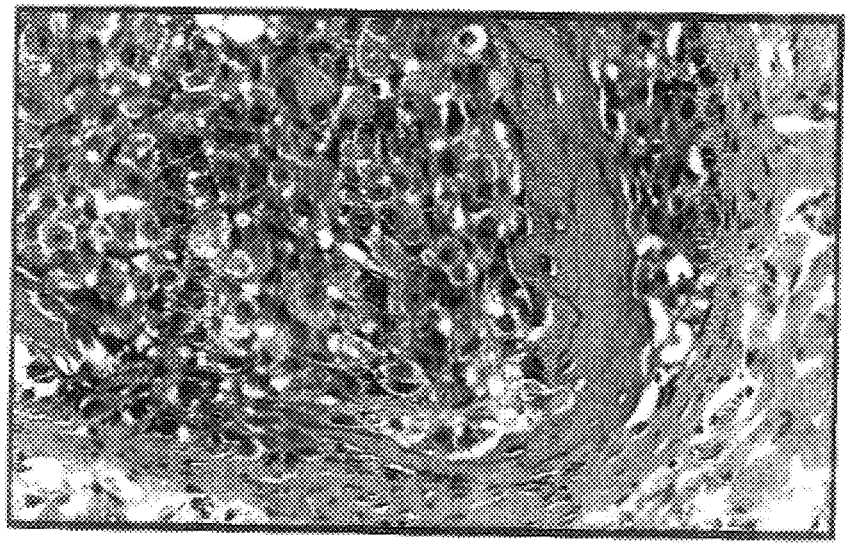
FIG. 5 shows histological analyses of infiltrated lesions of the NOG mice with U266 cells engrafted (magnified by 100 times).

FIGS. 2 to 5 show the histological analyses of infiltrated lesions of the NOG mice with U266 cells engrafted. As shown in FIG. 2 and FIG. 3 (magnified by 5.3 times and 12 times, respectively), U266 cells invade into the spinal cavity, accompanied by osteolytic lesions and extensive infiltration into surrounding muscles. As shown in FIG. 4 and FIG. 5 (magnified by 100 times), protean plasma cells invade into the spinal cavity.

Figure 6:
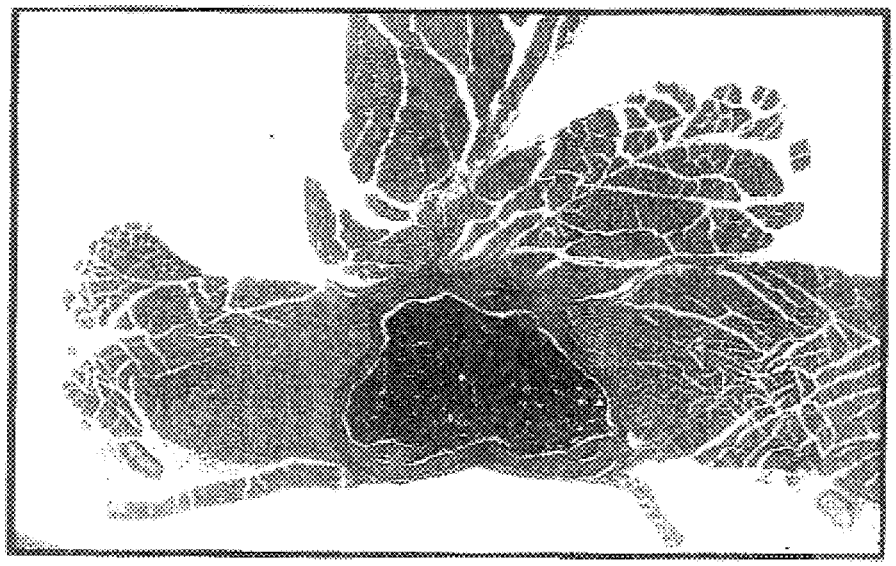
FIG. 6 shows histological analyses of bone marrow of the NOD/Shi-scid mice with U266 cells engrafted (magnified by 12 times).
Figure 7:
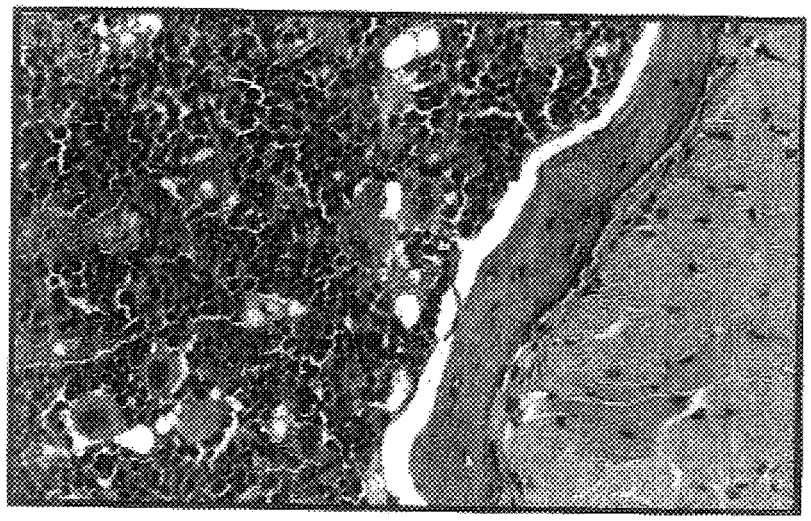
FIG. 7 shows histological analyses of bone marrow of the NOD/Shi-scid mice with U266 cells engrafted (magnified by 100 times).

FIG. 6 and FIG. 7 show the histological analyses of the bone marrow of the NOD/Shi-scid mice with U266 engrafted (magnified by 12 and 100 times, respectively). No infiltration of U266 cells into the bone marrow is observed in these figures.

Figure 8:
FIG. 8 shows histological analyses of bone marrow of the C.B-17/Icr-scid mice with U266 cells engrafted (magnified by 12 times).
Figure 9:
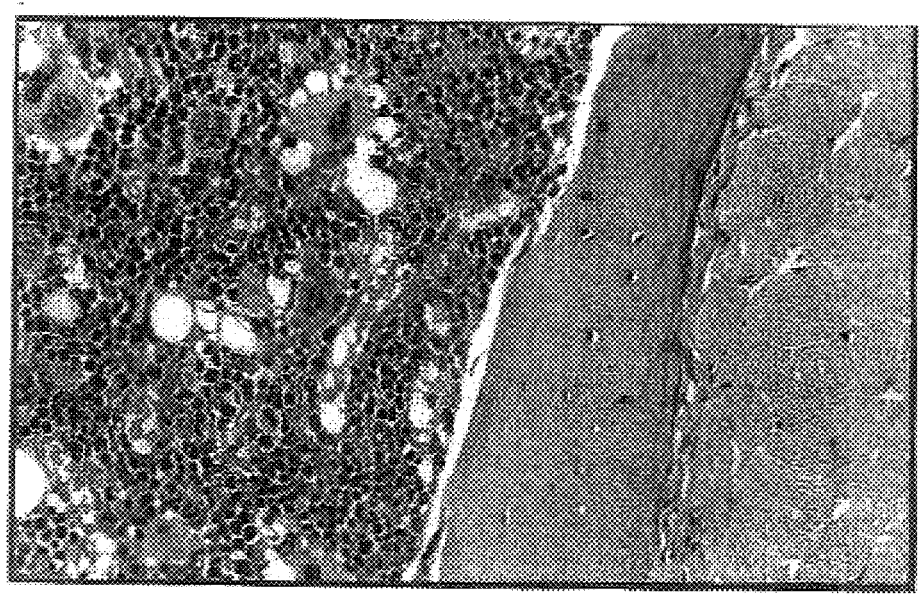
FIG. 9 shows histological analyses of bone marrow of the C.B-17/Icr-scid mice with U266 cells engrafted (magnified by 100 times).

FIG. 8 and FIG. 9 show the histological analyses of the bone marrow of the C.B-17/Icr-scid mice with U266 engrafted (magnified by 12 and 100 times, respectively). No infiltration of U266 cells into the bone marrow is observed in these figures.

Figure 10:
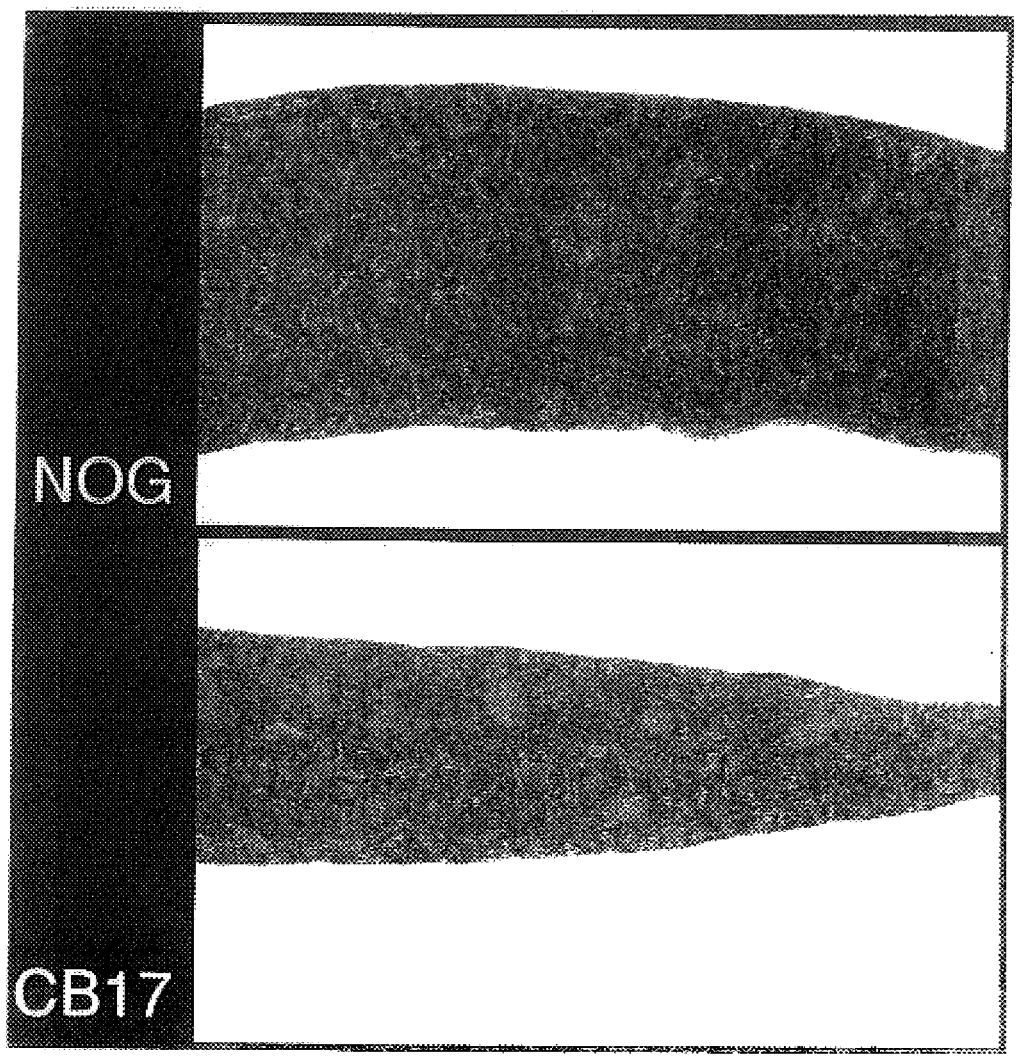
FIG. 10 shows histological analyses of spleens of NOG mice and C.B-17/Icr-scid mice.

FIG. 10 shows the histological analysis of the spleens of NOG mice and C.B-17/Icr-scid mice with U266 engrafted.

No infiltration of U266 cells into the spleen of NOG mice or C.B-17/Icr-scid mice is observed in this figure.

An average life span of NOG mice with U266 engrafted was about six weeks. U266 cells were confirmed to grow in bone marrow after engraftment even without irradiation.

All publications, patents and patent applications cited herein are incorporated herein by reference in their entirety.

INDUSTRIAL APPLICABILITY

As shown in Example 1, engrafted U266 cells were grown in bone marrow of NOG mice without rejection. The resultant NOG mice can, therefore, be used as an animal model for human multiple myeloma and applicable to pathological research for the disease and screening for the new anticancer drugs.

As shown in Example 2, engrafted lymphoma cells (LM-2-JCK) were grown in NOG mice without rejection. The resultant NOG mice can, therefore, be used as an animal model for human lymphoma and applicable to pathological research for the disease and screening for the new anticancer drugs.

The invention claimed is:

1. A method of creating a mouse model of human multiple myeloma, comprising a method engrafting human multiple myeloma U266 cells to NOG (NOD/Shi-scid, IL-2Rγ KO) mouse.

2. A NOG (NOD/Shi-scid, IL-2Rγ KO) mouse model in which human multiple myeloma U266 cells are engrafted and human multiple myeloma is formed.

3. A screening method of therapeutic agents for human multiple myeloma, which comprises administering a test substance to the human multiple myeloma mouse model according to claim 2.

* * * * *

UNITED STATES PATENT AND TRADEMARK OFFICE
CERTIFICATE OF CORRECTION

PATENT NO. : 7,259,290 B1
APPLICATION NO. : 10/533796
DATED : August 21, 2007
INVENTOR(S) : Miyakawa et al.

It is certified that error appears in the above-identified patent and that said Letters Patent is hereby corrected as shown below:

IN THE TITLE PAGE, item

(73) Assignee: should read as follows:

Central Institute For Experimental Animals – Kanagawa, Japan
  Keio University – Tokyo, Japan Signed and Sealed this Fourteenth Day of April, 2009

JOHN DOLL
*Acting Director of the United States Patent and Trademark Office*

SEQUENCE LISTING

```
<160> NUMBER OF SEQ ID NOS: 3

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence: Primer PI.

<400> SEQUENCE: 1
ctgctcagaa tgatgcctcc aattcc                                          26

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence: Primer PII.

<400> SEQUENCE: 2
cctgcgtgca atccatcttg ttcaat                                          26

<210> SEQ ID NO 3
<211> LENGTH: 24
<212> TYPE: DNA
<213> ORGANISM: Artificial Sequence
<220> FEATURE:
```

```
<223> OTHER INFORMATION: Description of Artificial Sequence: Primer
      PIII.

<400> SEQUENCE: 3
gatccagatt gccaaggtga gtag                                          24
```